United States Patent [19]
Saita et al.

[11] Patent Number: 4,842,848
[45] Date of Patent: Jun. 27, 1989

[54] MAKE-UP COSMETICS

[75] Inventors: Kenji Saita, Toyonaka; Kunio Saegusa, Niihama, both of Japan

[73] Assignee: Sumitomo Chemical Company, Limited, Osaka, Japan

[21] Appl. No.: 946,061

[22] Filed: Dec. 24, 1986

[51] Int. Cl.$^4$ ............................................. A61K 7/021
[52] U.S. Cl. ........................................ 424/63; 424/69; 424/401
[58] Field of Search ............................ 424/63, 69, 401

[56] References Cited

U.S. PATENT DOCUMENTS

| 2,034,697 | 3/1936 | Factor | 424/63 |
| 2,944,914 | 7/1960 | Bergosh | 424/63 X |
| 3,422,185 | 1/1969 | Kuritzkes | 424/63 |
| 3,951,679 | 4/1976 | Bernhard et al. | 424/63 X |
| 3,978,207 | 8/1976 | Fotiu et al. | 424/63 |
| 3,992,219 | 11/1976 | Clark | 106/291 |
| 4,119,712 | 10/1978 | Goldner et al. | 424/63 |
| 4,323,554 | 4/1982 | Bernhard | 424/63 |
| 4,373,963 | 2/1983 | Venishi et al. | 106/304 |
| 4,456,486 | 6/1984 | Bernhard | 424/63 X |
| 4,457,784 | 7/1984 | Bernhard | 424/63 X |
| 4,603,047 | 7/1986 | Watanabe et al. | 424/63 |

FOREIGN PATENT DOCUMENTS

| 0191292 | 8/1986 | European Pat. Off. | 424/63 |
| 1019666 | 1/1986 | Japan | 424/63 |
| 62-12711 | 1/1987 | Japan . | |

Primary Examiner—Ellis P. Robinson
Assistant Examiner—P. J. Ryan
Attorney, Agent, or Firm—Stevens, Davis, Miller & Mosher

[57] ABSTRACT

A new type of cosmetics is prepared by incorporating therein a synthetic flaky metallic oxide having an average thickness of about 0.1 to about 2 μm, an average size of about 1 to about 100 μm [which is defined as an average value of (the longest diameter of flakes+shortest diameter of flakes)/2 for 100 flakes], and a refractive index of about 1.4 to about 1.8. Make-up cosmetics containing an artificially synthesized flaky metallic oxide of a low refractive index as a pigment, particularly an extender pigment have an improved touch and stability with time in use which has not been attained by conventional cosmetics.

1 Claim, No Drawings

MAKE-UP COSMETICS

TECHNICAL FIELD

This invention relates to make-up cosmetics, more particularly to make-up cosmetics incorporating therein synthetic flaky metallic oxide having a specific size and a refractive index as a pigment.

Cosmetics are roughly classified into base cosmetics and make-up cosmetics.

Among them, make-up cosmetics aim at imparting a suitable coating and color to the skin, and specific examples thereof include powder foundation, oily foundation, pressed powder, lipstick, eye shadow and the like.

PRIOR ART

Make-up cosmetics comprise various base materials for coating the skin with moderate gloss and a feeling of transparency, improving spreadability (slip for face powder) and adherence, preventing make-up disorders due to secretions such as sweat, sebum and the like and further improving the touch in use and enhancing the moldability of products and colorants for coloring the skin.

Examples of base materials to be used include extender pigments such as talc and the like, a variety of raw materials such as fats or oils, hydrocarbons, surfactants or the like.

Various pigments known as extender pigments in said base materials have not been solely able to satisfy moderate gloss, spreadability and adhesiveness required as the extender pigments.

For example, talc, mica, kaolin, sericite and the like are known as natural-occurring laminar clay minerals. However, talc, mica and sericite have inferior adhesiveness, and kaolin, precipitated calcium carbonate and the like used for improving the adhesiveness have no spreadability. Therefore, they are combined and incorporated in foundation, face powder, compact face powder, lipstick, rouge and the like.

In the presence of fats or oil, perfumes and the like which are cosmetic ingredients, such clay minerals have problems to cause rancidity in the fats and oils and deterioration in perfumes because of impurities, hydroxyl groups, alkali metals and like contained therein. Although methods, which have been proposed for dehydrating clay minerals and incorporating the dehydrated clay minerals [Patent KOKAI (Laid-Open) No. 169412/82], treating clay minerals with a polyamino acid [Patent KOKAI (Laid-Open) No. 145006/82], require complicated processes, impurities cannot be completely removed. Furthermore, there are disadvantages in that clay minerals which must be white, by nature have a yellowish brown color due to such impurities (for example iron oxide).

Flaky pigments having thin layers of a metallic oxide having a high refractive index on platelet crystals of barium sulfate having a thickness of 0.05 to 1 μm (hereinafter abbreviated to μ) and a size of 5 to 100μ are proposed [Patent KOKAI (Laid-Open) No. 56833/73]. However, such pigments have disadvantages in that processes are long for depositing barium sulfate and then a metallic oxide, etc. and the resulting metallic oxide shines too much as an extender pigment because of pearly luster exhibited by the thin layers thereof having a thickness within the range of 0.01 to 0.1μ.

Furthermore, an attempt has been made to grind mica-titania ordinarily used as a pearl pigment, thereby to lower the luster for use as an extender pigment, but has a disadvantage of insufficient spreadability.

SUMMARY OF THE INVENTION

The present inventors have found out that an artificially synthesized flaky metallic oxide of low refractive index can be used as a pigment, particularly an extender pigment, and incorporated in make-up cosmetics thereby to give an improved touch and stability with time in use which has not been attained by the conventional cosmetics, thus this invention has been accomplished.

This invention relates to make-up cosmetics comprising an incorporated synthetic flaky metallic oxide having an average thickness of about 0.1 to about 2μ, an average size of about 1 to about 100μ and a refractive index of about 1.4 to about 1.8.

DISCLOSURE OF THE INVENTION

This invention will be explained in detail hereinafter.

Flakes generally vary in size and thickness, and the size is specified by an average size, i.e. average value of (the longest diameter of flakes+the shortest diameter thereof)/2 for 100 flakes. The thickness is also specified by an average thickness, i.e. average thickness for 100 flakes.

The synthetic flaky metallic oxide to be used in this invention has a refractive index of about 1.4 to about 1.8. This is because the refractive index of oils usually used for cosmetics is about 1.5 to about 1.6 and a marked deviation from such value deteriorates the feeling of transparency.

Examples of the metallic oxide having such refractive index include alumina (having a refractive index of 1.76), silica (1.40 to 1.55), magnesia (1.74) and like.

Mixed oxides comprising such metallic oxide may vary the refractive index optionally with the constituent ratio.

For example, the refractive index of a mixed oxide of alumina and silica is about 1.7 at a weight ratio of alumina to silica of 90/10 and about 1.65 at a weight ratio of 80/20. Even other metallic oxides, for example titania, zirconia or zinc oxide, having a high refractive index are usable depending on the ratio. For example, the refractive index of mixed oxide of titania and silica is about 1.8 at a weight ratio of titania to silica of 50/50 and about 1.6 at a weight ratio of 25/75.

If a moderate slight gloss is required, a rather high refractive index of about 1.6 to about 1.8 may be used. When it is desired to emphasize the feeling of transparency, a rather low refractive index may be used.

Natural products such as mica, talc, kaolin and the like have a refractive index near 1.5 with a narrow range, but the refractive index can easily be adjusted as described above by using such synthetic flaky metallic oxide.

The synthetic flaky metallic oxide to be used in this invention has an average thickness of about 0.1 to about 2μ and an average size of about 1 to about 100μ and assumes a moderate luster without turbidity.

If the average thickness is smaller than about 0.1μ, the reflectance is increased, and mechanical strength is deteriorated, resulting in brittleness.

The average thickness is about 0.1μ or above, preferably about 0.2μ or above.

If the average thickness is about 0.1μ or above, metallic luster is rapidly decreased and reduced to an exceedingly low value at an average thickness of about 0.2μ or above.

However, if the average thickness exceeds about 2μ, the adherence to the skin is lowered to deteriorate the feeling of use.

The average thickness is preferably about 2μ or below, more preferably about 1μ or below.

When the average size is smaller than about 1μ, moderate luster is lost, and the spreadability is completely lost though with good adherence, resulting in no feeling of transparency.

The spreadability is improved with increasing average size. However, if the average size exceeds about 100μ, particles tend to separate without accomplishing the object of coating the skin uniformly. Therefore, the average size is preferably about 100μ or below, more preferably about 40μ or below.

Accordingly, the flaky metallic oxide has preferably an average thickness of about 0.1 to about 2μ and an average size of about 1 to about 70μ, and more preferably an average thickness of about 0.2 to about 1μ and an average size of about 2 to about 40μ.

The synthetic flaky metallic oxide to be used in this invention can be produced by various processes.

For example, processes are cited for producing flaky alumina by reacting aluminum of high purity with mercury in the presence of hydrochloric acid, and then reacting the resulting product with hydrogen peroxide and an alcohol [Patent KOKAI (Laid-Open) No. 152999/75] or from acetic acid and hot aqueous solution of aluminum sulfate [patent KOKAI (Laid-Open) No. 24298/79], from an acyloxy group-containing metallic compound [Patent Application No. 31131/84], etc. Processes are cited for producing flaky silica by bringing calcium silicate into contact with a mineral acid [Patent KOKAI (Laid-Open) No. 118399/79], etc.

Examples of processes for preparing the flaky metallic oxide having a specific size include publicly known ones such as pulverization of said flaky metallic oxide obtained by the above-mentioned processes in a dry ball mill, wet ball mill, vibrating mill, roll mill, jet mill, etc. and/or combination of one or two more of classification steps such as a vibrating screen, a gyro sifter or hammer screen, wet classification methods such as a spiral classifier or hydraulic power classifier, dry classification methods such as dynamic or centrifugal air classifier or ore floatation methods and the like (Powder Engineering Handbook, edited by Kaichi Inoya, published by Asakura Publishing Co., Ltd.).

The proportion of formulation of the resulting flaky metallic oxide in make-up cosmetics is the same as that of the conventional extender pigments, and varies with the kind of cosmetics.

The flaky metallic oxide may be used, of course, with the conventional extender pigments and pearl pigments in combination.

Specifically, the proportion of the formulation is for example about 2 to about 60% by weight for oily foundation and about 20 to about 90% by weight for pressed powder and pressed foundation.

Generally, if the proportion of formulation is lower than described above the meritorious effects of this invention are not remarkable. If the proportion of formulation is higher than described above, make-up cosmetics comprise mostly powder with deteriorated touch in use such as deterioration of moist feeling.

Furthermore, the synthetic flaky metallic oxide may be coated with colorants, for example colored metallic oxides such as iron oxide, chromium oxide or cobalt oxide; metal complex salts such as iron cyanide; colored metal hydroxides such as iron hydroxide; organic dyes such as Red No. 2 or Yellow No. 4 and organic pigments such as aluminum lakes of the organic dyes and the like to form colored extender pigments for use.

Such flaky metallic oxides may be formulated in cosmetics by the well-known mixing methods, i.e. a Henschel mixer, ribbon mixer, V-type blender and the like.

EXAMPLES

This invention is described in more detail by way of Examples which follow:

Values of light reflectance (higher values indicate that the luster is close to metallic luster) were measured by the following methods:

Measurement of reflectance

Pigment materials were formulated in nitrocellulose lacquer to give a proportion of 10% by weight, and the following test liquid was obtained

| Pigment material | 10 parts by weight |
| Nitrocellulose RS 1/4 | 16 parts by weight |
| Isopropyl alcohol | 7 parts by weight |
| Isoamyl acetate | 35 parts by weight |
| n-Butyl acetate | 29 parts by weight |
| Diethylene glycol monobytyl ether | 3 parts by weight |

The resulting liquid was thoroughly dispersed and mixed and fixed on a platen. The liquid was then spread into a layer having a thickness of 75μ on a black-and-white hiding power chart with a doctor blade, and solidified to form a film.

The surface gloss of the film on the black part on the chart was determined by measurement at an angle of incidence of 20 degrees and an angle of reflection of 20 degrees according to the method of measuring the specular gloss described in JIS-Z8741.

The resulting surface gloss was used as the reflectance.

(The reflectance of sericite, talc, etc. which are the conventional extender pigments is within the range of 5 to 30%.)

The reflectance of the flaky metallic oxide of this invention is shown in Table 1, and reflectances of the conventional pigment materials are listed in Table 2. The size and thickness of particles were measured with a scanning electron microscope.

Organoleptic tests were carried out on spreadability, adherence, smoothness, gloss and color tone of cosmetics by 20 women to make evaluation using the 5 rating method wherein the highest score is 5.

TABLE 1

| Sample No. | Flaky metallic oxide Kind | Refractive index | Average size of flakes (μ) | Average thickness of flakes (μ) | Reflectance (%) |
| --- | --- | --- | --- | --- | --- |
| 1 | Silica | 1.47 | 10 | 0.5 | 3.8 |
| 2 | Silica | Same as above | 20 | 0.5 | 6.8 |
| 3 | Silica | Same as above | 40 | 0.5 | 17 |
| 4 | Silica | Same as above | 80 | 0.9 | 25 |
| 5 | Magnesia | 1.74 | 10 | 0.5 | 6.2 |
| 6 | Alumina | 1.76 | 10 | 0.5 | 6.2 |

TABLE 2

(Reflectance of pigments)

| Name of pigment | Shape | Reference (%) |
| --- | --- | --- |
| DM-OA mica | Flake | 23.2 ± 0.3 |
| Sericite FSE | Flake | 13.4 ± 0.2 |
| Fine powdery talc | Flake | 5.1 ± 0.2 |
| Powdery titanium oxide (A-100, manufactured by Ishihara Sangyo Co., Ltd.) | Powder | 22.1 ± 0.3 |

EXAMPLE 1 AND COMPARATIVE EXAMPLES 1 AND 2

To a 40% by weight solution of tetraethyl orthosilicate in ethanol, was added formic acid in twice molar amount based on Si in said solution. The resulting solution was mixed at 70° C. for 3 hours under stirring, and a piece of cleaned slide glass was dipped therein, pulled up at a speed of 75 cm/min and 200 cm/min and dried at 90° C. for 30 minutes in an air bath to obtain transparent flakes having smooth surfaces, an average size of 100μ and an average thickness of 1.7μ under the former conditions and an average size of 105μ and an average thickness of 3.5μ under the latter conditions. The flaking ratio was 100%.

The resulting flakes were fired at 450° C. for 30 minutes to obtain transparent flaky silica having a refractive index of 1.48 and an average size of 60μ and an average thickness of 0.9μ under the former conditions and an average size of 62μ and an average thickness of 2.8μ under the latter conditions. The above-mentioned transparent flaky silica was then ultrasonically pulverized to give flaky silica having an average size of 35μ and an average thickness of 0.9μ [flaky silica (A)] and flaky silica having an average size of 37μ and an average thickness of 2.8μ [flaky silica (B)].

These flaky silicas were used to prepare powder foundations.

For purpose of comparison, a powder foundation comprising formulated talc was prepared. The results obtained are shown in Table 3.

As can be seen from Table 3, the formulation of the flaky silicas has better adherence, slip and gloss than those of talc.

EXAMPLE 2 AND COMPARATIVE EXAMPLES 3 AND 4

Into a glass beaker, was put 200 ml of 1 N AlCl$_3$ solution, and the solution was stirred with a magnetic stirrer. To the stirred solution, was added 170 ml of 1 N NaOH solution at a rate of 3 ml/min by means of a micro tube pump. After completing the addition, the mixture was stirred for another 30 minutes to give a white gel of pH 7.1.

The resulting gel was centrifuged at 1000 rpm for 10 minutes to discard the supernatant. Distilled water was added to the resulting precipitates to make up the total volume to 200 ml. After thorough stirring, the mixture was centrifuged to discard the supernatant, and the same operation was repeated further twice.

Distilled water was added to the resulting precipitates to make up the total volume to 200 ml. The mixture was aged at room temperature for 1 week and then centrifuged at 5000 rpm for 5 minutes to discard the supernatant, and precipitates were washed with ethanol and vacuum-dried to obtain 1.57 g of white powder.

The above-mentioned powder was then heated in steam atmosphere at 300° C. for 8 hours and then fired at 1000° C. for 1 hour to obtain flaky alumina having a size of 1.5 to 200μ, a thickness of 0.05 to 2μ and a refractive index of 1.7, which was sorted out to give only flakes having a size within the range of 10 to 50μ in a zigzag classifier. The resultant flakes had a thickness of 0.05 to 0.5μ and were designated as flaky alumina A.

Flakes having a size within the range of 100 to 200μ were further sorted out, and the thickness thereof was 1 to 2μ. The resulting flakes were designated as flaky alumina B.

Such flaky aluminas A and B were used to prepare oily foundations.

For purposes of comparison, an oily foundation comprising formulated kaolin was prepared. The results obtained are shown in Table 4.

EXAMPLE 3 AND COMPARATIVE EXAMPLE 5

To a mixture solution of 100 g of 40% by weight solution of tetraethyl orthosilicate in ethanol and 200 g of 40% by weight solution of aluminum isopropoxide in isopropanol, was added 43 g of propionic acid. The resulting solution was mixed at 70° C. for 3 hours under stirring, and a piece of cleaned slide glass was then dipped therein, pulled up at a speed of 50 cm/min, dried at 90° C. for 30 minutes in an air bath and fired at 450° C. for 30 minutes to obtain transparent flaky silica-alumina having an average size of 30μ, an average thickness of 0.5μ and a refractive index of 1.57, which was further ultrasonically pulverized and levigated to give an average size of 10μ.

The resultant flaky silica alumina was used to prepare face powder.

For purposes of comparison, talc was used to prepare face powder. The results obtained are shown in Table 5.

TABLE 3

(Powder foundation)

| Composition (% by weight) | | Example 1 | Comparative Example 1 | Comparative Example 2 |
| --- | --- | --- | --- | --- |
| Flaky silica (A) | | 68 | 0 | 0 |
| Flaky silica (B) | | 0 | 68 | 0 |
| Mica | | 0 | 0 | 50 |
| Talc | | 0 | 0 | 18 |
| Titanium dioxide | | 8 | 8 | 8 |
| Iron oxide | | 4 | 4 | 4 |
| Liquid paraffin | | 15 | 15 | 15 |
| Lanolin | | 3 | 3 | 3 |
| Sorbitan sesquioleate | | 2 | 2 | 2 |
| Perfume | | Slight amount | Slight amount | Slight amount |
| Evaluation method | Spreadability | 4.6 | 4.2 | 4.2 |
| | Adherence | 4.5 | 3.0 | 4.0 |
| | Gloss | 4.7 | 4.0 | 3.7 |
| | Color tone | 4.8 | 4.5 | 3.1 |

TABLE 4

(Oily foundation)

| Composition (% by weight) | Example 2 | Comparative Example 3 | Comparative Example 4 |
| --- | --- | --- | --- |
| Flaky alumina A | 21.0 | 0.0 | 0.0 |
| Flaky alumina B | 0.0 | 21.0 | 0.0 |
| Kaolin | 0.0 | 0.0 | 15.0 |

TABLE 4-continued (Oily foundation)

| Composition (% by weight) | | Example 2 | Comparative Example 3 | Comparative Example 4 |
|---|---|---|---|---|
| Talc | | 0.0 | 0.0 | 6.0 |
| Titanium oxide | | 10.0 | 10.0 | 15.0 |
| Color pigment | | 4.0 | 4.0 | 4.0 |
| Liquid paraffin | | 27.5 | 27.5 | 27.5 |
| Isopropyl palmitate | | 15 | 15 | 15 |
| Lanolin alcohol | | 2 | 2 | 2 |
| Microcrystalline wax | | 7 | 7 | 7 |
| Ozokerite | | 8 | 8 | 8 |
| Candelilla wax | | 0.5 | 0.5 | 0.5 |
| Perfume | | Slight amount | Slight amount | Slight amount |
| Evaluation method | Spreadability | 4.8 | 4.0 | 4.2 |
| | Adherence | 4.5 | 2.0 | 4.0 |
| | Gloss | 4.7 | 4.3 | 3.8 |
| | Color tone | 4.9 | 4.8 | 3.0 |

After keeping the above-mentioned products warm at 37° C. for 1 month, a deteriorated odor of the perfume and rancid smell of the fat and oil were perceived in Comparative Example 4. However, there was no change in Example 2.

Comparative Example 3 had improved color sensation and gloss, but considerably inferior slip and adherence.

TABLE 5

(Face powder)

| Composition (% by weight) | Example 3 | Comparative Example 5 |
|---|---|---|
| Flaky silica-alumina | 65 | 0 |
| Talc | 0 | 65 |
| Kaolin | 15 | 15 |
| Precipitated calcium carbonate | 5 | 5 |
| Iron oxide | 0.7 | 0.7 |
| Titanium dioxide | 1 | 1 |
| Zinc stearate | 3 | 3 |
| Zinc oxide | 8.3 | 8.3 |
| Squalane | 2 | 2 |
| Perfume | Slight | Slight |

TABLE 5-continued (Face powder)

| Composition (% by weight) | | Example 3 | Comparative Example 5 |
|---|---|---|---|
| Preservative | | Slight amount | Slight amount |
| Evaluation method | Spreadability | 4.6 | 4.2 |
| | Adherence | 4.5 | 3.0 |
| | Gloss | 4.9 | 4.0 |
| | Color tone | 4.9 | 4.5 |

MERITORIOUS EFFECTS OF THE INVENTION

The synthetic flaky metallic oxide of this invention exhibits a moderate gloss comparable to that of talc and sericite, spreadability comparable to that of talc, mica and sericite, better adherence than that of talc, mica and sericite and better spreadability than that of kaolin and precipitated calcium carbonate, and further is chemically stable and not easily deteriorated.

Cosmetics comprising such synthetic flaky metallic oxide formulated therein satisfy adherence, spreadability and moderate gloss at the same time and give unprecedented smooth and moist touch and impart natural beautiful finish by moderate slight gloss.

For some kind of cosmetics, the reflectance of the synthetic flaky metallic oxide may be moderately changed, thus varying glossiness and feeling of transparency with ease.

What is claimed is:

1. In a make-up cosmetic comprising conventional base materials, the improvement comprising having incorporated in said make-up cosmetic at least one synthetic flaky oxide compound consisting essentially of alumina, silica or magnesia, or comprising a mixture of at least one synthetic flaky oxide compound consisting essentially of alumina, silica or magnesia, and at least one synthetic flaky oxide compound consisting essentially of tiatania, zirconia or zinc oxide, the flakes of said flaky oxide or flaky oxide mixture having an average thickness of 0.1 to 2 μm and an average size of 1 to 100 μm and a refractive index of 1.4 to 1.8, said average size being defined herein as an average value of the longest diameter of flakes plus the shortest diameter thereof divided by 2 for 100 flakes.

* * * * *